(12) United States Patent
Carey

(10) Patent No.: US 8,163,310 B2
(45) Date of Patent: Apr. 24, 2012

(54) PLANT INVIGORATOR

(76) Inventor: Vincent Priaulx Carey, Guernsey (GB)

( * ) Notice: Subject to any disclaimer, the term of this patent is extended or adjusted under 35 U.S.C. 154(b) by 215 days.

(21) Appl. No.: 12/604,667

(22) Filed: Oct. 23, 2009

(65) Prior Publication Data

US 2010/0130360 A1    May 27, 2010

Related U.S. Application Data

(63) Continuation-in-part of application No. 10/474,265, filed as application No. PCT/GB01/01584 on Apr. 6, 2001, now abandoned.

(51) Int. Cl.
*A01N 65/00* (2009.01)
*A01N 25/00* (2006.01)

(52) U.S. Cl. ......................... 424/725; 514/783

(58) Field of Classification Search .................. None
See application file for complete search history.

(56) References Cited

U.S. PATENT DOCUMENTS 4,066,786 A    1/1978 Bent et al.

FOREIGN PATENT DOCUMENTS

| EP | 0 862 861 | 9/1998 |
|---|---|---|
| EP | 0 998 850 | 5/2000 |
| JP | 2000-198703 | 7/2000 |
| JP | 2002-201101 | 7/2002 |
| WO | WO 98/00023 | 1/1998 |

OTHER PUBLICATIONS

CFR—Code of Federal Regulations Title 21, Chapter 1—Food and Drug Administration Department of Health and Human Services, Subchapter B—Food for Human Consumption, part 169—Food Dressings and Flavorings, Subpart B—Requirements for Specific Standardized Food Dressings and Flavorings, Apr. 1, 2009, vol. 21, http://www.accessdata.fda.gov/scripts/cdrh/cfdocs/cfcfr/CFRSearch.cfm?fr=169.175.
Dignum, Mark J.W. et al., Food Chemistry, Identification of Glucosides in Green Beans of Vanilla Planifolia Andrews and Kinetics of Vanilla β-glucosidase, Apr. 2004, pp. 199-205, vol. 85, Issue 2, Science Direct, http://www.sciencedirect.com/science?_ob=ArticleURL&_udi=B6T6R-4B1XSKG-2&_u . . . .
Japanese Official Examination Report (dated Jan. 4, 2011).

*Primary Examiner* — Alton Pryor
(74) *Attorney, Agent, or Firm* — Fitch Even Tabin & Flannery LLP

(57) ABSTRACT

A plant invigorator which may contain the following ingredients per litre: 10%-33% anion surfactants; 5%-18% nonionic surfactants; 2%-20% ethanol or methylated spirits or cider vinegar; 25%-60% de-mineralised aqueous solution; 0.01 ml-4 ml natural extract such as vanilla, almond or strawberry; 0.01-5 grams food grade coloring; 0.01-5 grams lanolin or 0.5 ml-15 ml glycerine or 0.5 ml to 5 ml paraffin oil.

16 Claims, 2 Drawing Sheets

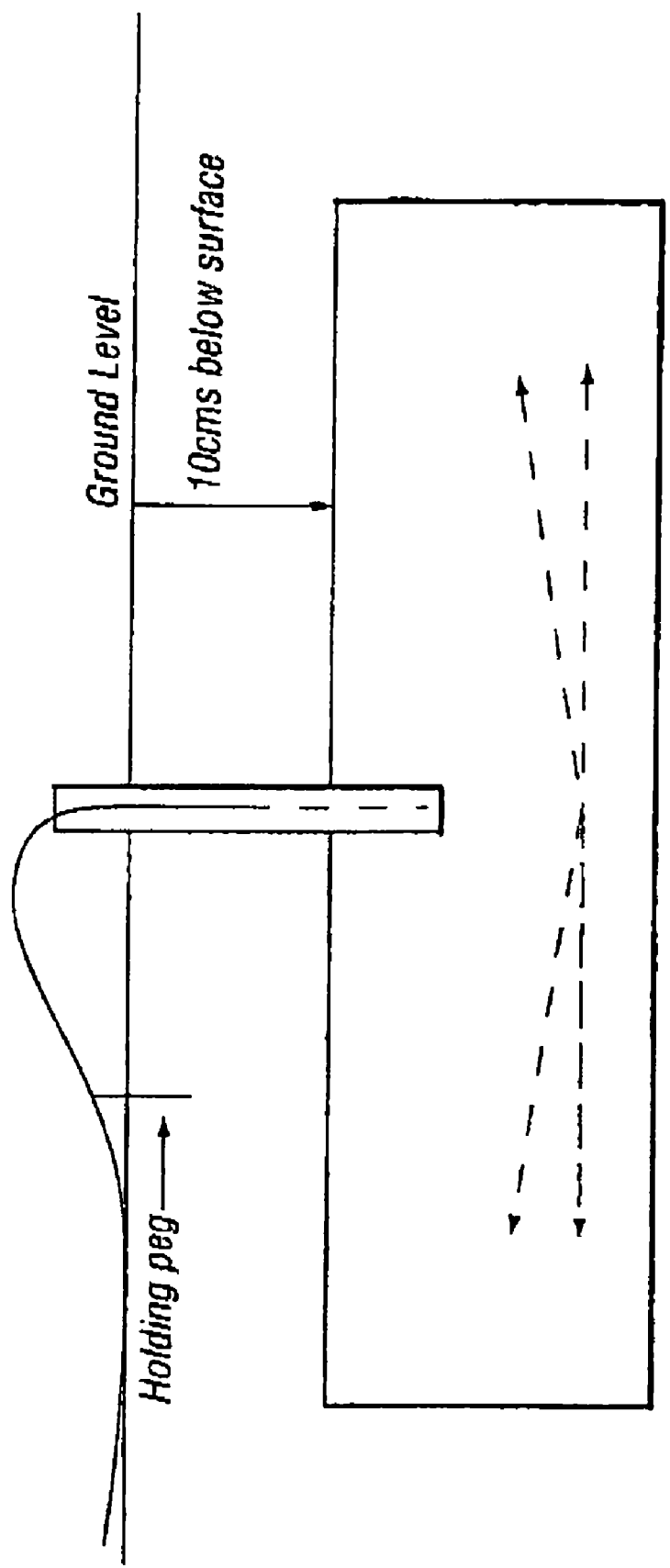

PLANT INVIGORATOR

CLAIM OF PRIORITY

The present application is a continuation-in-part of, and claims priority to, U.S. patent application Ser. No. 10/474,265 filed on Oct. 6, 2003 now abandoned, which is a 35 USC 371 National stage entry of PCT/GB2001/001584 filed Apr. 6, 2001, the entire contents of each are herein incorporated by reference for all purposes.

FIELD OF THE INVENTION

The present invention relates to a plant invigorator.

It has been previously proposed to use a variety of chemicals to invigorate plant growth thus maximising yield and production. Such plant invigorators have been used to treat plants with regard to a variety of infestations.

It is the aim of the present invention to provide an invigorator, which enables crops to be safely treated with regard to a variety of insect and fungus infestations.

The plant invigorator according to the present invention has the advantage that it can be used to treat crops with regard to controlling sucking insects and treating fungus. However, it does not have an adverse effect with regard to the digestive systems of humans or animals. Furthermore, the invigorator has the advantage that when it is treating specific crop types additional additives can be added to further improve development.

Preferably the plant invigorator of the present invention can contain one or more of the following ingredients in the following ranges:

50-350 grams urea (N) 46%,
5-60 grams iron chelates 13.2%.

This composition has the advantage of improving the vigour and greeness of the crop.

Embodiment can contain the following ingredients per litre in the following ranges:
a. 10%-33% anion surfactants,
b. 5%-18% non-ionic surfactants,
c. 2%-20% ethanol or methylated spirits or cider vinegar,
d. 25%-60% de-mineralized aqueous solution,
e. 0.01 ml-4 ml of a natural extract (also known as essence in the United Kingdom)
f. 0.01-1 grams coloring—food grade,
g. 0.01-5 grams lanolin or 0.5 ml-15 ml glycerine or 0.5 ml to 5 ml paraffin oil.

The natural extract can be those found in the art for vanilla, almond, strawberry, and the like. Extracts are known in the art and treated by the FDA under, for example, Title 21, Part 169.175 for vanilla. Further, extracts, such as vanilla extract, are known to contain catalytic enzyme glycosides (see, for example, EP0620982 and Food Chemistry Volume 85, Issue 2, April 2004, Pages 199-205, "Identification of glucosides in green beans of Vanilla planifolia Andrews and kinetics of vanilla β-glucosidase", Mark J. W. Dignuma, Rob van der Heijdenb, Josef Kerlerc, Chris Winkelc and Rob Verpoorte.) The food grade coloring is any coloring non-toxic colouring that is safe for use on edible plants and crops.

Advantageously, any one or more of the ingredients in combinations and ranges listed below can also be added to the mixture depending on the needs of the crop concerned:

20-150 grams potassium,
10-150 grams phosphate,
10-110 grams magnesium,
0.5-1 gram manganese,
0.5-1 gram boron,
0.2-0.5 gram molybdenum,
0.2-0.5 gram zinc,
1-3 grams copper,
0.1-0.5 gram cobalt, and
5-40 millimols per litre o-acetoxybenzoic acid.

Advantageously the invigorator contains
25% anion surfactants,
13% non-ionic surfactants,
13% ethanol,
40% de-mineralised aqueous solution,
0.15 ml catalytic enzyme glycosides extract vanilla,
0.14 grams colouring food grade (BP),
0.19 grams lanolin,
260 grams urea (N) 46%, and
40 grams iron chelates 13.2%.

Preferably the invigorator can contain about 16% anion surfactants, 8% non-ionic surfactants, 8% ethanol, 58% de-mineralised aqueous solution, 0.08 ml natural extract, 0.055 grams colouring food grade (BP), 0.12 grams lanolin, 170 grams urea (N) 46%, and 25 grams iron chelates 13.2%.

As an example of one embodiment of the present invention, one such invigorator composition can contain:

20% anion surfactants,
10% non-ionic surfactants,
10% ethanol,
50% de-mineralised aqueous solution,
0.1 ml catalytic enzyme glycosides extract vanilla,
0.075 grams colouring food grade (BP),
0.153 grams lanolin,
220 grams urea (N) 46%, and
30 grams iron chelates 13.2%.

Preferably the plant invigorator is used to control whitefly, aphids, mealy bug, scaly insects, leaf hopper, and baby thrip.

In a preferred embodiment the plant invigorator can be used to control red spider, botrytis and powdery mildew.

Advantageously the plant invigorator is used to invigorate roses, freesias, astroemeria, herbs, tomatoes, capsicums and strawberries.

Further nutrients can be added to the invigorator comprising potassium, phosphate, magnesium, manganese, boron, molybdenum, zinc, copper and cobalt depending upon the needs of the plants concerned.

Examples of treatment of crops with the invigorator will now be described in relation to the preferred embodiment given above.

EXAMPLE 1

Crop: Strawberries
Media: Peat Modules Hanging
Sprayed ×3 Dates: 11.03.01
15.03.01
19.03.01

Crop was heavily infested with whitefly and aphid species. First spray achieved 90% plus kill of both whitefly and aphid. Second and third sprays achieved 100% kill of whitefly and only a small percent of aphid not accessible to spray surviving.

EXAMPLE 2

Crop: Commercial roses

The crop prior to the first application of the invigorator had whitefly adults and eggs, red spider mite, baby and adult thrip, powdery mildew and botrytis.

Crop vigour was also a problem due to poor light levels.

After the first application, the invigorator knocked out all the adult whitefly and some eggs, and partial killed the red spider adults and about 60% of the eggs. It dried out the mildew and botrytis. It cleared the baby thrip on the stems completely but it did not affect the adult thrips.

On the second application a total wipe out on the whitefly and red spider was achieved and no evidence of baby thrip or mildew to be found. Some adult thrips remained.

EXAMPLE 3

Crop: 1.4 acres of Freesias under glass
3 sprays of the Invigorator at 3 weekly intervals.
Sprayed ×3 Dates: Wednesday 24 Jan. 2001
Wednesday 14 Feb. 2001
Wednesday 7 Mar. 2001

The plant invigorator was used in a 0.8 acre block of metal glass and a 0.6 acre block of wooden glass of commercial freesias. Twelve (12) varieties of freesias were being grown. The freesia crop was about 3 weeks away from picking at the first spray.

The crop was assessed prior to the first spray and assessed once a week for nine weeks commencing 3 days after the first spray.

There were small pockets of aphid present and very little botrytis before the first spray. The crop looked healthy, although a slightly lighter green due to the poor light levels.

The first spray killed all aphids present and dried up the botrytis. The crop also responded favourably to the Nitrogen and Iron and looked a more lush darker green.

No aphid was seen after the first spray and botrytis was virtually non-existent. The botrytis spores were not spreading, although circulating fans were on day and night for the full trial period. The heating boilers were set to come on only if the temperature dropped below 3° C., basically frost protection only. Usually more botrytis would have been evident because of the damp conditions outside and the fact that heat was not being applied.

Two small blocks adjacent to the trial block where the Invigorator was not used had a lot more botrytis present and Elvaron, a fungicide for botrytis, had to be applied on 3 occasions.

EXAMPLE 4

Two preliminary trials were carried out using the Invigorator to assess the effects of the product on protected roses, in particular, to quantify the effect on whitefly and red spider mite. The product was applied to both leaf surfaces using conventional hydraulic spray equipment at the rate of 1 litre of product/500 litres of water. A 3-spray programme was used with spray intervals of approximately 3 days.

Site 1

La Moye Roses

The whitefly prone cv Kiss was used in the trial. Unfortunately the first spray had been applied before the first leaf samples were taken. A random sample of middle leaves was taken after the first spray and after the last spray to quantify the effects of the treatment. Ten terminal leaflets were viewed under the microscope and pest counts completed.

The first spray had killed most of the adult whitefly; additional sprays did not significantly improve this visual effect. There was no obvious phytotoxicity to the crop. There was a positive improvement in leaf quality with the leaves a darker green and the absence of the normal stickiness associated with whitefly epidemics. There was also evidence that the sooty mould development was reduced.

| 1 spray | | | 3 spray | | |
|---|---|---|---|---|---|
| Eggs | | | Eggs | | |
| Live | Dead | Empty | Live | Dead | Empty |
| 296 | 211 | 1023 | 266 | 131 | 1514 |
| Larvae | | | Larvae | | |
| Live | | Dead | Live | | Dead |
| 291 | | 196 | 325 | | 642 |
| Pupae | | | Pupae | | |
| Live | Dead | Emerged | Live | Dead | Emerged |
| 120 | 24 | 73 | 31 | 3 | 48 |

The product appeared to have a significant effect on the larval stage rather than the egg and pupal stage. Eggs that had started to hatch were affected and the emerging larval were mostly killed.

Site 2

Franc Fief Vinery

The trial was carried out on the cv Bianca which had a significantly high level of whitefly and some red spider mite. The previous 2 treatments were based on Chess a new aphicide/whitefly insecticide. The grower noted a significant knockdown of the adult population after the first spray of the Invigorator. He also noted that the leaves were cleaner with spray deposit and sooty mould reduced after the treatments. However, the flowers may have been affected by the spray because the petals were sticking together and failing to unfold.

| No sprays | | | Two sprays | | | Three sprays | | |
|---|---|---|---|---|---|---|---|---|
| Eggs | | | Eggs | | | Eggs | | |
| Live | Dead | Empty | Live | Dead | Empty | Live | Dead | Empty |
| 373 | 75 | 1544 | 1449 | 42 | 1360 | 401 | 17 | 2607 |
| Larvae | | | Larvae | | | Larvae | | |
| Live | | Dead | Live | | Dead | Live | | Dead |
| 665 | | 372 | 396 | | 419 | 112 | | 811 |
| Pupae | | | Pupae | | | Pupae | | |
| Live | Dead | E-merged | Live | Dead | E-merged | Live | Dead | E-merged |
| 146 | 0 | 36 | 5 | 3 | 100 | 23 | 19 | 25 |

Again, the product gave a significant reduction in the number of larvae.

This site also had an infestation of red spider mite. The whole block received one Invigorator treatment. A smaller area within the block received a further 2 sprays whereas the remainder had a treatment based on Aseptacarex and Applaud. This allowed a direct comparison on red spider mite control as Aseptacarex is an acaricide.

|  | % adults/larvae | |
| --- | --- | --- |
|  | Live | Dead |
| 3x Invigorator | 17 | 83 |
| 1x Invigorator + Aseptacarex + Applaud | 53 | 47 |

The Invigorator programme gave a significant increase in red spider mite activity compared with the Aseptacarex.

As can be seen, the Invigorator proved to be an effective treatment for the control of adult whitefly. A single spray gave a high knockdown of the adult population.

A second aspect of the present invention relates to water retaining means.

It has previously been proposed to provide compost and other materials to retain water, which can also be altered so that it contains nutrients and such like.

Furthermore, it has been proposed to provide compost and such material in PVC bags for growing plants in for instance on the patio of a house.

It is an aim of the present invention to provide a water retaining means which retains a high level of moisture and nutrient and is suitable for use in temperate and arid conditions. Accordingly the present invention is directed to water retaining means which for a volume of 13,800 $cm^3$ contains the following ingredients:

a. 6-12.5 litres of one of the following coco compost (Coir), peat, bark, rockwool, glasswool, wood shavings, purlite, vermiculite, composted waste
  b. 0-140 grams=0-50% volume of dry shredded paper,
  c. 10-250 grams copolymer acrylamide acrylate of reticulated sodium
  d. 10-200 grams disodium ferric diethylenetriamine penta-acetic acid (FeDTPA) (7% Iron as Fe).
  e. 50-400 grams Ureaform (38% N),
  f. 20-300 grams ammonium nitrate (34.5% N),
  g. 5-50 grams monopotassium phosphate
  h. 5-30 grams trace elements (Fe, Mn, Zn, Cu, B, Mo, K) in a suitable base, the means being further equipped with an irrigation pipe.

This provides the advantage that the water retaining means can be buried in soil or sand near a shrub, tree or bush to provide a source of water and nutrient.

Furthermore when the means is buried watering is possible through the irrigation pipe with the result that water is held in the container not on the surface.

Preferably the irrigation pipe is a solid PVC pipe, metal pipe or flat plastics material tube with holes.

The irrigation pipe tube is connected to one inlet which can irrigate a number of containers. If several containers are placed around a single shrub, bush or tree or several shrubs, bushes or trees these can be watered by one inlet.

Preferably the contents of the means can be retained using compressed coir, peat, bark, rockwool, wood shavings, purlite, vermiculite or composted waste.

Preferably the means are retained by a container.

This provides the advantage of better retaining the moisture in the means.

Advantageously the container can be made from any one of the following materials; polythene, polypropylene, plastics material, board, cardboard, wood, and paper.

Advantageously the container is made of cardboard, this provides the advantage that it is biodegradable.

In a preferred embodiment the water retaining means can contain:
  a. 12.5 litres of coco compost (Coir),
  b. 70 grams-25% volume of dry shredded paper,
  c. 50 grams copolymer acrylamide acrylate of reticulated sodium,
  d. 50 grams disodium ferric diethylenctriamine penta-acetic acid (FeDTPA),
  e. 200 grams Ureaform,
  f. 100 grams Nitram ammonium nitrate,
  g. 15 grams monopotassium phosphate, and
  h. 10 grams trace elements.

The container when in use is preferably sited some ten centimetres below the sand/soil surface and the irrigation pipe sticks up through the surface to allow irrigation.

Examples of use of the container will now be given below:
  amending soilless composts,
  amending soils for planting beds and such like, transplanting rooted cuttings, seedlings and bedding plants, and transplanting trees and shrubs.

An example of a water retaining means made in accordance with the present invention comprises a 400 mm×300 mm×115 mm (external measurement) container made of test board, which contains:

1. 12.5 litres of coco compost (Coir),
  2. 70 grams-25% volume of dry shredded paper,
  3. 50 grams Supersorb (composition: copolymer acrylamide acrylate of reticulated sodium),
  4. 50 grams Librel Fe-DP Chelate (7% Iron as Fe, chemical name: Disodium Ferric Diethylenctriamine Penta-Acetic Acid (FeDTPA)),
  5. 200 grams Nitroform (chemical name: Ureaform-38% N),
  6. 100 grams Nitram (chemical name: Ammonium nitrate-34.5% N),
  7. 15 grams Monopotassium Phosphate (technical grade), and
  8. 10 grams Frit 253 trace elements and is equipped with a PVC irrigation pipe which protrudes from its top.

The cardboard box can vary in length, width and depth: e.g. 1: 200 mm×150 mm×80 mm (external measurements)-2,400 $cm^3$ or 2: 1200 mm×900 mm×345 mm (external measurements)-372,600 $cm^3$.

The cardboard can be thicker or thinner: e.g. 1: 112/112/112 (single or double fluting) or 2: 300/200/300 (single fluting) or 3: 300/150/300 (double fluting).

The container is designed primarily to aid the transformation of desert areas into lush green plantations. Its main role is to conserve water and to provide protection for the sand or soil surrounding the root zone area of trees, bushes, shrubs and plants by keeping it moist and cool.

The container incorporates a mix formulated for desert regions, which keeps the container in a state of controlled dampness to create a cooling effect and ready availability of nutrients whenever water is applied directly on to the container. This also keeps the roots of the plant healthy and stops aggravation by dryness or salt scorch through lack of correct systematic watering.

The container's ultimate aim is that of water conservation and green and healthy growth. A blend of natural coir, a long lasting effective soil improver, which contains 60% natural lignin mixed with capillary matrix, is used. The container has a formulated mix of NPK plus trace elements, with extra nitrogen added to overcome nitrogen starvation that may result from bacterial activity which can cause "nitrogen fixation".

The container eventually breaks down fulfilling its secondary role in tightening up the sand/soil and building up the structure for better water and nutrient retention.

The working life of a container is approximately 3 years, this is due to the ability of being able to regulate the breakdown period of this special mix. The nutrient period lasts approximately 12 months, however nutrient levels can be easily topped up cost effectively over the remaining life of the container.

The container has the following advantages that it is biodegradable, reduces volume and frequency of watering, greatly reduces water evaporation, slow release nutrient feed system, green and healthy growth stimulant, helps to keep sand/soil cool and moist, lowers pH and controls temperature around the root zone, long lasting effective sand/soil improver, improves aeration and structure of soil, encourages microbial population activity, and nutrient levels can be easily topped up.

The container can also be used on existing areas of trees, bushes and shrubs to encourage a healthier growth and conserve vast amounts of precious water. This will enable more areas to be planted without using extra water.

FIG. 2 shows the container when positioned for use so that the top of the container is approximately 10 cm below sand/soil level.

Figure 1A:
FIG. 1a shows two containers positioned around a small to medium sized bush or shrub.
Figure 1A:
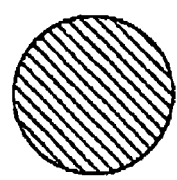
Figure 1A:
Figure 1B:
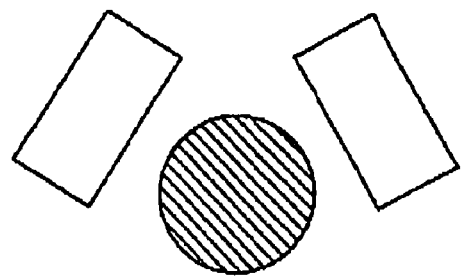
FIG. 1b shows three containers positioned around a small tree of large bush or shrub.
Figure 1B:
Figure 1C:
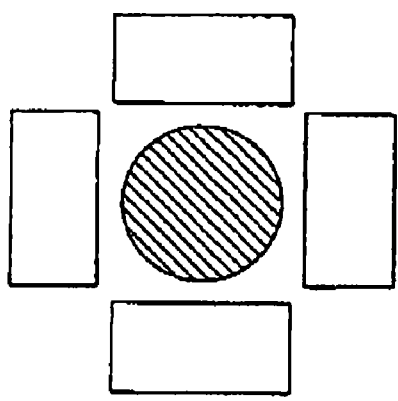
FIG. 1c shows four containers positioned around a medium sized tree.
Figure 1D:
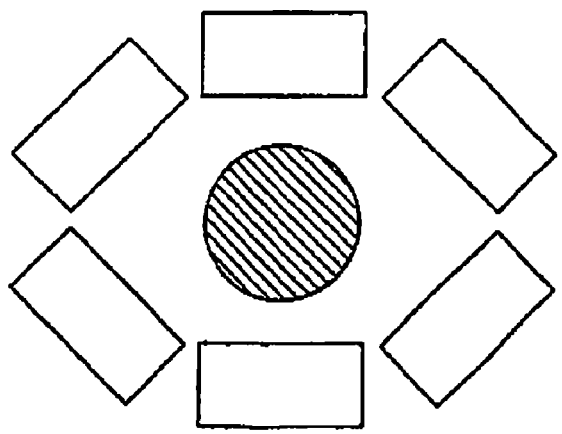
FIG. 1d shows six containers positioned around a large tree.

The irrigation pipe protrudes through the soil or sand surface. The relevant irrigation section is connected up. Each container receives at least 12 litres of water at first watering so it is well saturated.

After 1 year a mixture of nutrients can be added to each container to maintain green plantations. The irrigation nozzle is removed, nutrient tablets are dropped into tube, which are then, pushed into container with a plunger and the irrigation nozzle replaced. This process should be repeated every six months throughout the remaining 2 year life of the container.

What is claimed is:

1. A plant invigorator composition which contains the following ingredients per litre:
   10%-33% anion surfactants,
   5%-18% non-ionic surfactants,
   2%-20%-ethanol or methylated spirits or cider vinegar,
   25%-60% de-mineralised aqueous solution,
   0.01 ml-4 ml natural extract,
   0.01-1 grams coloring food grade, and
   0.01-5 grams lanolin or 0.5 ml-15 ml glycerine or 0.5 ml to 5 ml paraffin oil.

2. The plant invigorator composition according to claim 1, which additionally contains one or both of the following ingredients per litre:
   50-350 grams urea (N) 46%, and
   5-60 grams iron chelates 13.2%.

3. The plant invigorator composition according to claim 2, which contains per litre:
   20% anion surfactants,
   10% non-ionic surfactants,
   10% ethanol,
   50% de-mineralised aqueous solution,
   0.2 ml vanilla extract containing catalytic enzyme glycosides,
   0.075 grams food grade coloring,
   0.153 grams lanolin,
   220 grams urea (N) 46%, and 30 grams iron chelates 13.2%.

4. The plant invigorator composition according to claim 1, which additionally contains 20-150 grams potassium.

5. The plant invigorator composition according to claim 1, which additionally contains 10-150 grams phosphate.

6. The plant invigorator composition according to claim 1, which additionally contains 10-110 grams magnesium.

7. The plant invigorator composition according to claim 1, which additionally contains 0.5-1 gram manganese.

8. The plant invigorator composition according to claim 1, which additionally contains 0.5-1 gram boron.

9. The plant invigorator composition according to claim 1, which additionally contains 0.2-0.5 gram molybdenum.

10. The plant invigorator composition according to claim 1, which additionally contains 0.2-0.5 gram zinc.

11. The plant invigorator composition according to claim 1, which additionally contains 1-3 grams copper.

12. The plant invigorator composition according to claim 1, which additionally contains 0.1-0.5 gram cobalt.

13. The plant invigorator composition according to claim 1, which additionally contains 5-40 millimols per litre o-acetoxybenzoic acid.

14. The plant invigorator composition according to claim 1, which is used to control whitefly, aphids, mealy bug, scale insects, leaf hopper, baby thrip.

15. The plant invigorator composition according to claim 1, which is used to control red spider, botrytis and powdery mildew.

16. The plant invigorator composition according to claim 1, which is used to invigorate roses, freesias, astroemeria, herbs, tomatoes, capsicums and strawberries.

* * * * *